United States Patent [19]

Bacon et al.

[11] Patent Number: 5,260,478

[45] Date of Patent: Nov. 9, 1993

[54] IODINATED AROYLOXY CARBOXAMIDES

[75] Inventors: Edward R. Bacon, East Greenbush; Sol J. Daum, Albany, both of N.Y.; Carl R. Illig, Phoenixville, Pa.

[73] Assignee: Sterling Winthrop Inc., New York, N.Y.

[21] Appl. No.: 986,646

[22] Filed: Dec. 8, 1992

[51] Int. Cl.$^5$ .............................................. C07C 69/76
[52] U.S. Cl. ........................................ 560/110; 424/5
[58] Field of Search .......................... 560/110; 424/5; 514/535, 532

[56] References Cited

U.S. PATENT DOCUMENTS 5,055,451 10/1991 Krantz et al. ................... 560/110

FOREIGN PATENT DOCUMENTS 3038598 5/1982 Fed. Rep. of Germany .
1129154 6/1986 Japan .

Primary Examiner—Paul J. Killos
Attorney, Agent, or Firm—William J. Davis

[57] ABSTRACT

Compounds having the structure

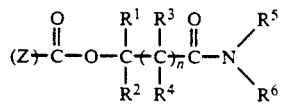

wherein
  $(Z)\!\!-\!\!COO$ is the residue of an iodinated aromatic acid;
  n is an integer from 0 to 20;
  $R^1$ and $R^2$ are independently H, alkyl, fluoroalkyl, cycloalkyl, aryl, aralkyl, alkoxy or aryloxy;
  $R^3$ and $R^4$ are independently a substituent as defined for $R^1$ and $R^2$ above, halogen, hydroxy or acylamino;
  and $R^5$ and $R^6$ are independently H, alkyl, cycloalkyl, aryl, aralkyl, alkoxy, alkoxyalkyl, or acetamidoalkyl;
  or $R^5$ and $R^6$, taken together with the nitrogen atom to which they are attached, represent a 4 to 7-membered nitrogen containing ring, are useful as contrast agents in x-ray imaging compositions and methods.

8 Claims, No Drawings

IODINATED AROYLOXY CARBOXAMIDES

FIELD OF INVENTION

This invention relates to iodinated aroyloxy carboxamides which are particularly useful as contrast agents for x-ray imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, *Pharmaceuticals in Medical Imaging,* 1990, MacMillan Publishing Company.

Various soluble and water insoluble iodinated amides and esters have been used as x-ray contrast agents. For example, U.S. Pat. No. 3,097,228 describes derivatives of 2,4,6-triiodobenzoyloxyalkanoic acids having the structure

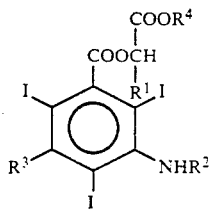

wherein $R^1$ is H or lower alkyl, $R^2$ is H or alkanoyl, $R^3$ is H or alkanoylamino, and $R^4$ is lower alkyl. However, there is no suggestion of a carboxamide group linked to an ester group on an iodinated aromatic ring.

U.S. Pat. No. 4,328,202 describes ionic 5-C-substituted 2,4,6-triiodoisophthalic acid derivatives as x-ray contrast agents, but does not suggest a carboxamide group linked to an ester group on an iodinated aromatic acid.

U.S. Pat. No. 4,364,921 describes triiodinated isophthalic acid diamides as nonionic x-ray contrast media, but does not suggest a carboxamide group linked to an ester group on an iodinated aromatic ring.

EP-A 498,482 describes nanoparticulate x-ray contrast compositions which have proven to be extremely useful in medical imaging. However, particulate contrast agents in certain in vivo applications can exhibit less than fully satisfactory enzymatic degradation, e.g., in plasma and blood.

It would be desirable to provide compounds for use as x-ray contrast agents having improved enzymatic degradability and appropriate solubility profiles.

SUMMARY OF THE INVENTION

We have discovered and prepared novel iodinated aroyloxy carboxamides which are useful as contrast agents in x-ray contrast compositions.

More specifically, in accordance with this invention, there are provided compounds having the structure

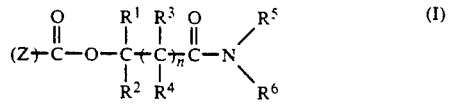

wherein
($Z \rightarrow COO$ is the residue of an iodinated aromatic acid;
n is an integer from 0 to 20;
$R^1$ and $R^2$ are independently H, alkyl, fluoroalkyl, cycloalkyl, aryl, aralkyl, alkoxy or aryloxy;
$R^3$ and $R^4$ are independently a substituent as defined for $R^1$ and $R^2$ above, halogen, hydroxy or acylamino;
and $R^5$ and $R^6$ are independently H, alkyl, cycloalkyl, aryl, aralkyl, alkoxy, alkoxyalkyl, or acetamidoalkyl;
or $R^5$ and $R^6$, taken together with the nitrogen atom to which they are attached, represent a 4 to 7-membered nitrogen containing ring.

This invention further provides an x-ray contrast composition comprising the above-described compound and a method for medical x-ray diagnostic imaging which comprises administering to the body of a mammal a contrast effective amount of the above-described x-ray contrast composition.

It is an advantageous feature of this invention that novel compounds are provided which find particular utility as x-ray contrast agents.

It is another advantageous feature of this invention that compounds are provided having appropriate solubility profiles and improved enzymatic degradability.

DESCRIPTION OF PREFERRED EMBODIMENTS

In structural formula I above, ($Z \rightarrow COO$ is the residue of an iodinated aromatic acid. The iodinated aromatic acid can comprise one, two, three or more iodine atoms per molecule. Preferred species contain at least two, and more preferably, at least three iodine atoms per molecule. The iodinated compounds can contain substituents which do not deleteriously effect the contrast enhancing capability of the compound.

Illustrative examples of suitable aromatic acids include
diatrizoic acid,
metrizoic acid,
urokonic acid,
iothalamic acid,
trimesic acid,
ioxaglic acid (hexabrix),
ioxitalamic acid,
tetraiodoterephthalic acid,
iodipamide, and the like.
In preferred embodiments, ($Z \rightarrow COO$ is the residue of a substituted triiodobenzoic acid such as an acyl, carbamyl, and/or acylamino substituted triiodobenzoic acid.

$R^1$ and $R^2$ independently represent H; substituted or unsubstituted, linear or branched alkyl, preferably containing from 1 to 20, more preferably 1 to 8 carbon atoms such as methyl, ethyl, propyl, isopropyl, butyl, pentyl, hexyl and the like; fluoroalkyl, preferably containing from 1 to 3 fluorine atoms, the alkyl portion of which is as described for $R^1$ above; cycloalkyl, preferably containing from 3 to 8 carbon atoms such as cyclopropyl and cyclobutyl; aryl, preferably containing from 6 to 10 carbon atoms, such as phenyl and naphthyl; aralkyl, preferably containing from 7 to 12 carbon atoms, such as benzyl; alkoxy, the alkyl portion of which contains from 1 to 20 carbon atoms as described above; or aryloxy, the aryl portion of which preferably contains from 6 to 10 carbon atoms as described above.

$R^3$ and $R^4$ independently represent a substituent as defined for $R^1$ above, halogen, such as chlorine or bromine, hydroxy, or acylamino, i.e., a

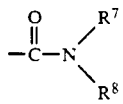

group wherein $R^7$ and $R^8$ are as defined for $R^5$ below. However, reactive substituents such as halogen are not preferred on the carbon atom adjacent to the amide carbonyl.

Rhu 5 and $R^6$ independently represent H, alkyl as defined for $R^1$ above; cycloalkyl as defined for $R^1$ above; aryl as defined for $R^1$ above, aralkyl as defined for $R^1$ above; alkoxy as defined for $R^1$ above; alkoxyalkyl, the alkyl portions of which are, as defined for $R^1$ above; acetamidoalkyl, i.e.,

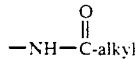

wherein alkyl is as defined for $R^1$ above; or $R^5$ and $R^6$, taken together with the nitrogen atom to which they are attached, represent a 4 to 7 membered saturated or unsaturated nitrogen containing ring such as piperidyl, piperizinyl, pyrrolidinyl and the like.

The alkyl, cycloalkyl, aryl, aralkyl and alkoxy groups and the nitrogen containing ring in structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine, bromine and iodine, acylamino, carboalkoxy, carbamyl and the like. However, reactive substituents such as halogen, hydroxy and acylamino are not preferred on the carbon atoms, if present in $R^5$ and $R^6$ adjacent to the amide nitrogen.

The compounds of this invention can be prepared by reacting the carboxylate of an iodinated aromatic acid with a functionalized amide having the formula

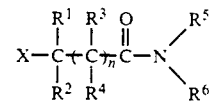

wherein X is a leaving group and $R^1$-$R^6$ are as defined above. Suitable leaving groups include halogen, such as Br, I and Cl, sulfonyloxy, such as methanesulfonyloxy and toluenesulfonyloxy. When X=Cl, it has been found that the addition of NaI can facilitate the reaction. The carboxylates of iodinated aromatic acids and functionalized amides useful as the starting materials in the preparation of the compounds of this invention are known compounds and/or can be prepared by techniques known in the art. For example, suitable amides include commercially available bromoacetamide and chloroacetamide derivatives as exemplified below. A general reaction scheme is as follows:

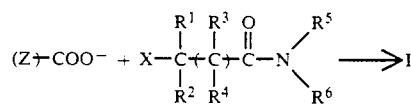

The reaction can take place between $-78°$ C. and $100°$ C. For convenience, the reaction can take place at ambient temperature.

For convenience, the reaction can take place at ambient pressure, however, higher and lower pressures are contemplated.

The following are specific illustrative examples of preferred compounds of this invention that have been prepared:

2-amino-2-oxoethyl 3,5-bis(acetylamino)-2,4,6-triiodobenzoate (WIN 65,540), 2-ethylamino-2-oxoethyl 3,5-bis(acetylamino)-2,4,6-triiodobenzoate (WIN 65,312), 2-diethylamino-2-oxoethyl 3,5-bis(acetylamino)-2,4,6-triiodobenzoate (WIN 67,499), 2-dibutylamino-2-oxoethyl 3,5-bis(acetylamino)-2,4,6-triiodobenzoate (WIN 67,774), 2-diisopropylamino-2-oxoethyl 3,5-bis(acetylamino)-2,4,6-triiodobenzoate (WIN 67,901), 2-bis(2-hydroxyethyl)amino-2-oxethyl 3,5-bis-(acetylamino)-2,4,6-triiodobenzoate (WIN 67,862), 2-diethylamino-2-oxoethyl 3,5-bis(diacetylamino)-2,4,6-triiodobenzoate (WIN 68,187), and 2-bis(2-acetoxyethyl)amino-2-oxoethyl 3,5-bis(diacetylamino)-2,4,6-triiodobenzoate (WIN 67,888).

These preferred compounds of this invention conform to structure I above, wherein $R^1$-$R^2$=H and n=0 as indicated below:

| WIN | Z | $R^5$ | $R^6$ |
|---|---|---|---|
| 65,540 | CH₃CONH–[triiodophenyl]–NHCOCH₃ (with I at 2,4,6 positions) | H | H |
| 65,312 | " | H | $C_2H_5$ |
| 67,499 | " | $C_2H_5$ | $C_2H_5$ |
| 67,774 | " | $C_4H_9$ | $C_4H_9$ |
| 67,901 | " | $CH(CH_3)_2$ | $CH(CH_3)_2$ |
| 67,862 | " | $CH_2CH_2OH$ | $CH_2CH_2OH$ |

-continued

| WIN | Z | R⁵ | R⁶ |
| --- | --- | --- | --- |
| 67,888 | 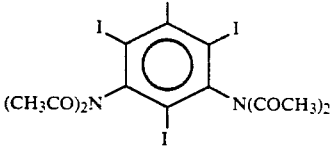 | CH₂CH₂OCOCH₃ | CH₂CH₂OCOCH₃ |
| 68,187 | " | C₂H₅ | C₂H₅ |

When used as an x-ray contrast agent, the compound of this invention preferably comprises at least about 35%, more preferably 40% iodine by weight.

In preferred embodiments, the compounds of this invention can be formulated into particulate x-ray contrast compositions, preferably nanoparticulate x-ray contrast compositions, as described in commonly-owned EPO 498, 482, the disclosure of which is hereby incorporated by reference in its entirety. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1-99.9, preferably 2-45 and more preferably 10-25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5-20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool, liver, spleen and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Preparation of WIN 65, 540

Bromoacetamide (21 76 g, 157.8 mmol) was added to a solution of sodium diatrizoate (100.3 g, 157.8 mmol) in 1000 ml of dry dimethylformamide and the solution was stirred at ambient temperature under an argon atmosphere for approximately 12 hr. The reaction mixture was then concentrated under vacuum to give a residue which was taken up in cold water. The solid product was collected, washed with water, and air dried to give a white solid. This crude product was taken up in 350 ml of saturated aqueous sodium bicarbonate and the mixture was stirred for 15 min. The product was collected, washed successively with water, methanol and ether and dried to give 92.4 g (88%) of the desired product. Recrystallization from DMF-H$_2$O gave analytically pure material, mp 288°–300° C. (decomp.) after drying at 120° C. under high vacuum; CI-MS: MH+ 672. The $^1$H-NMR (300 MH$_z$) spectral data was consistent with the desired product. Calculated for C$_{13}$H$_{12}$I$_3$N$_3$O$_5$: C 23.27, H 1.80, I 56.74, N 6.26, Found: C 23.34, H 1.64, I 56.78, N 6.27.

EXAMPLES 2–5

The following compounds were synthesized using a procedure similar to that described in Example 1 above for preparing WIN 65,540, except that in these preparations, the following chloroacetamide derivatives were used in place of bromoacetamide, sodium iodide was added as a catalyst, and the reactions were heated on a steam bath for 2 hours after stirring for 12 hours overnight at room temperature.

| Example | WIN | Chloroacetamide Derivative | % Yield |
|---|---|---|---|
| 2 | 67,774 | ClCH$_2$CON(C$_4$H$_9$)$_2$ | 92 |
| 3 | 67,499 | ClCH$_2$CON(C$_2$H$_5$)$_2$ | 83 |
| 4 | 67,901 | ClCH$_2$CON(CH(CH$_3$)$_2$)$_2$ | 92 |
| 5 | 67,862 | ClCH$_2$CON(CH$_2$CH$_2$OH)$_2$ | 94 |

EXAMPLE 6

Preparation of WIN 67, 888

Acetic anhydride (100 ml) was added to a solution of WIN 67,862 (20.3 g, 26.7 mmol) prepared as described above in dry pyridine (200 ml) and the mixture was stirred for 12 hr at ambient temperature. The solution was then added to excess ice-water and the precipitated solid was collected and washed with water. The crude product (20.5 g, 88%) was recrystallized from ethyl acetate to give analytically pure material, mp 178°–180° C., after drying under vacuum; CI-MS: MH+ 928. The $^1$H-NMR (300 MH$_z$) spectral data was consistent with the proposed structure. Calculated for C$_{25}$H$_{28}$I$_3$N$_3$O$_{11}$: C 32.38, H 3.04, I 41.06, N 4.53; Found: C 32.41, H 2.95, I 41.25, N 4.39.

EXAMPLE 7

Preparation of WIN 68,187

WIN 68,187 was synthesized using a procedure similar to that described in Example 6 for preparing WIN 67,888, except that acetic anhydride was added to a solution of WIN 67,499.

The invention has been described in detail with particular reference to certain preferred embodiments thereof, but it will be understood that variations and modifications can be effected within the spirit and scope of the invention.

We claim:

1. A compound having the structure

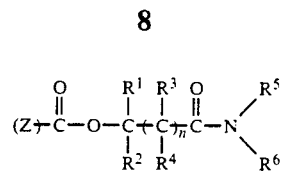

wherein (Z⊕COO is the residue of an iodinated aromatic acid;

n is an integer from 0 to 20;

R$^1$ and R$^2$ are independently H, alkyl, fluoroalkyl, cycloalkyl, aryl, aralkyl, alkoxy or aryloxy;

R$^3$ and R$^4$ are independently a substituent as defined for R$^1$ and R$^2$ above, halogen, hydroxy or acylamino;

and R$^5$ and R$^6$ are independently H, alkyl, cycloalkyl, aryl, aralkyl, alkoxy, alkoxyalkyl, or acetamidoalkyl;

or R$^5$ and R$^6$, taken together with the nitrogen atom to which they are attached, represent a 4 to 7-membered nitrogen containing ring.

2. The compound of claim 1 wherein (Z⊕COO is the residue of an iodinated aromatic acid selected from:
diatrizoic acid,
metrizoic acid,
urokonic acid,
iothalamic acid,
trimesic acid,
ioxagalic acid,
ioxitalamic acid,
tetraiodoterephthalic acid and
iodipamide.

3. The compound of claim 1 wherein (Z⊕COO is the residue of diatrizoic acid.

4. The compound of claim 1 wherein n=0, R$^1$=H and R$^2$=H.

5. The compound of claim 1 selected from the group consisting of 2-amino-2-oxoethyl 3,5-bis(acetylamino)-2,4,6-triiodobenzoate, 2-ethylamino-2-oxoethyl 3,5-bis(acetylamino)-2,4,6-triiodobenzoate, 2-diethylamino-2-oxoethyl 3,5-bis(acetylamino)-2,4,6-triiodobenzoate, 2-dibutylamino-2-oxoethyl 3,5-bis(acetylamino)-2,4,6-triiodobenzoate, 2-diisopropylamino-2-oxoethyl 3,5-bis(acetylamino)-2,4,6-triiodobenzoate, 2-bis(2-hydroxyethyl)amino-2-oxethyl 3,5-bis-(acetylamino)-2,4,6-triiodobenzoate, 2-diethylamino-2-oxoethyl 3,5-bis(diacetylamino)-2,4,6-triiodobenzoate, and 2-bis(2-acetoxyethyl)amino-2-oxoethyl 3,5-bis(-diacetylamino)-2,4,6-triiodobenzoate.

6. An x-ray contrast composition comprising the compound of claim 1.

7. The x-ray contrast composition of claim 6 further including a pharmaceutically acceptable carrier.

8. A method for medical x-ray diagnostic imaging which comprises administering to the body of a mammal a contrast effective amount of the x-ray contrast composition of claim 6.

* * * * *